United States Patent
Nakazawa et al.

(10) Patent No.: US 8,158,787 B2
(45) Date of Patent: Apr. 17, 2012

(54) PROCESS FOR PRODUCING TRICHLOROPYRIMIDINE COMPOUND

(75) Inventors: Koichi Nakazawa, Toyonaka (JP); Tomonori Yoshiyama, Funabashi (JP); Kouji Yoshikawa, Toyonaka (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 394 days.

(21) Appl. No.: 12/532,683

(22) PCT Filed: Mar. 26, 2008

(86) PCT No.: PCT/JP2008/056505
§ 371 (c)(1),
(2), (4) Date: Sep. 23, 2009

(87) PCT Pub. No.: WO2008/117884
PCT Pub. Date: Oct. 2, 2008

(65) Prior Publication Data
US 2010/0160630 A1    Jun. 24, 2010

(30) Foreign Application Priority Data
Mar. 28, 2007 (JP) ................. 2007-083954

(51) Int. Cl.
C07D 239/24    (2006.01)
(52) U.S. Cl. .................................................. 544/316
(58) Field of Classification Search .................. 544/316
See application file for complete search history.

(56) References Cited

U.S. PATENT DOCUMENTS

| | | | |
|---|---|---|---|
| 4,642,398 A | 2/1987 | Cantrell |
| 5,696,301 A | 12/1997 | Harada et al. |
| 6,187,952 B1 | 2/2001 | Pfirmann et al. |
| 2004/0092402 A1 | 5/2004 | Kuragano et al. |

FOREIGN PATENT DOCUMENTS

| | | | |
|---|---|---|---|
| EP | 826674 A1 | 3/1998 |
| JP | 63-502181 T | 8/1988 |
| JP | 10-500668 T | 1/1998 |
| WO | 95/26330 A1 | 10/1995 |
| WO | 97/30965 A1 | 8/1997 |
| WO | 2007/126142 A1 | 11/2007 |

OTHER PUBLICATIONS

Richard C. Larock; "Comprehensive Organic Transformations : A Guide to Functional Group Preparations"; 2nd Edition; pp. 619-622, 689-693, 703; (1999).
H. Gershon et al., "Pyrimidines. IV. 2-, 5-, and 2,5-Substituted Chloropyrimidines", Journal of Medicinal Chemistry, vol. 7, No. 6, pp. 808-811, (1964).
J. Chesterfield et al., "Pyrimidines, Part VIII. Halogeno- and Hadrazino-pyrimidines.", Journal of Chemical Society, pp. 3478-3481, (1955).

*Primary Examiner* — James O Wilson
*Assistant Examiner* — Ebenezer O Sackey
(74) *Attorney, Agent, or Firm* — Panitch Schwarze Belisario & Nadel LLP

(57) ABSTRACT

A process for producing a trichloropyrimidine compound represented by the formula (2):

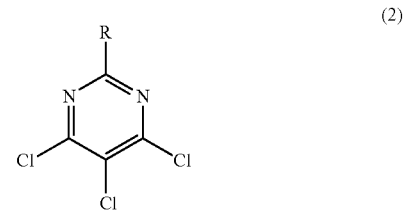

(2)

wherein R represents a hydrogen atom etc., comprising reacting a dihydroxypyrimidine compound represented by the formula (1):

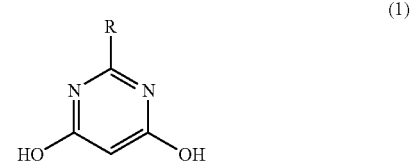

(1)

wherein R represents the same meaning as above, with sulfuryl chloride and at least one chlorinating agent selected from the group consisting of hydrogen chloride, thionyl chloride, phosgene, phosphorus oxychloride, phosphorus pentachloride and phosphorus trichloride in the presence of an organic base.

10 Claims, No Drawings

PROCESS FOR PRODUCING TRICHLOROPYRIMIDINE COMPOUND

CROSS-REFERENCE TO RELATED APPLICATION

This application is a Section 371 of International Application No. PCT/JP2008/056505, filed Mar. 26, 2008, which was published in the Japanese language on Oct. 2, 2008 under International Publication No. WO 2008/117884 A1, and the disclosure of which is incorporated herein by reference.

TECHNICAL FIELD

The present invention relates to a process for producing a trichloropyrimidine compound.

BACKGROUND ART

EP 826674 A1 and US 2004/92402 A1 disclose that trichloropyrimidine compounds are useful as intermediates of pharmaceuticals and agrichemicals of psychotropic drugs and herbicides.

As a process for producing the trichloropyrimidine compound, a process comprising reacting 4,6-dihydroxypyrimidine with iodine chloride to obtain 5-chloro-4,6-dihydroxypyrimidine followed by reacting obtained 5-chloro-4,6-dihydroxypyrimidine with phosphorus oxychloride is described in Journal of Chemical Society, 3478 (1955).

US 2004/9240 A1 discloses a process comprising reacting 4,6-dihydroxypyrimidine with hydrogen chloride to obtain 4-chloro-6-hydroxypyrimidine, and reacting obtained 4-chloro-6-hydroxypyrimidine with antiformin to obtain 4,5-dichloro-6-hydroxypyrimidine followed by reacting obtained 4,5-dichloro-6-hydroxypyrimidine with thionyl chloride.

DISCLOSURE OF THE INVENTION

The present invention provides
<1> A process for producing a trichloropyrimidine compound represented by the formula (2):

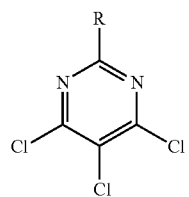

(2)

wherein R represents a hydrogen atom; a halogen atom; a mercapto group; a cyano group; a nitro group; an alkyl group which may be substituted with at least one substituent selected from the group consisting of a halogen atom, a C3-C6 cycloalkyl group, a C6-C14 aryl group, a C3-C8 heteroaryl group, a C1-C3 alkoxy group, a C1-C3 alkylthio group, a C6-C14 arylthio group, a cyano group, a nitro group, a C2-C14 disubstituted amino group and a C2-C14 disubstituted carbamoyl group; an alkoxy group; an alkenyl group; an alkynyl group; an aryl group which may be substituted with at least one substituent selected from the group consisting of a C1-C6 alkyl group, a C2-C4 alkenyl group, a C5-C6 cycloalkyl group, a halogen atom, a C1-C3 alkoxy group, a C2-C4 alkynyl group, a C2-C14 disubstituted amino group, a nitro group, a cyano group and a C2-C14 disubstituted carbamoyl group; or a heteroaryl group which may be substituted with at least one substituent selected from the group consisting of a C1-C4 alkyl group, a benzyl group, a C6-C10 aryl group, a halogen atom, a C1-C3 alkoxy group, a nitro group, a cyano group and a C2-C14 disubstituted amino group (hereinafter, simply referred to as the trichloropyrimidine compound (2)), comprising reacting a dihydroxypyrimidine compound represented by the formula (1):

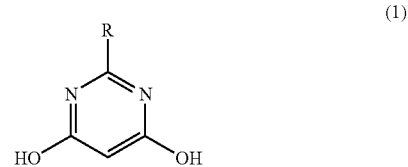

(1)

wherein R represents the same meaning as above (hereinafter, simply referred to as the dihydropyrimidine compound (1)), with sulfuryl chloride and at least one chlorinating agent selected from the group consisting of hydrogen chloride, thionyl chloride, phosgene, phosphorus oxychloride, phosphorus pentachloride and phosphorus trichloride in the presence of an organic base;

<2> The process according to the above <1>, wherein the dihydroxypyrimidine compound represented by the formula (1) is reacted with sulfuryl chloride, and the obtained reaction mixture or a treated material thereof is reacted with at least one chlorinating agent selected from the group consisting of hydrogen chloride, thionyl chloride, phosgene, phosphorus oxychloride, phosphorus pentachloride and phosphorus trichloride in the presence of an organic base;

<3> The process according to the above <1> or <2>, wherein the organic base is triethylamine;

<4> The process according to the above <2>, wherein the reaction of the dihydroxypyrimidine compound represented by the formula (1) and sulfuryl chloride is conducted in the presence of an organic solvent;

<5> The process according to the above <4>, wherein the organic solvent is chlorobenzene;

<6> The process according to any of the above <1> to <5>, wherein the chlorinating agent is phosphorus oxychloride;

<7> The process according to any of the above <1> to <6>, wherein R is a hydrogen atom.

BEST MODE FOR CARRYING OUT THE PRESENT INVENTION

First, the dihydroxypyrimidine compound (1) will be illustrated.

Examples of the halogen atom include a fluorine atom, a chlorine atom, a bromine atom and an iodine atom. Examples of the alkyl group include a liner or branched chain C1-C6 alkyl group such as a methyl group, an ethyl group, an n-propyl group, an isopropyl group, an n-butyl group, an isobutyl group, a sec-butyl group, a tert-butyl group, an n-pentyl group and an n-hexyl group.

The alkyl group may be substituted with at least one substituent selected from the group consisting of a halogen atom, a C3-C6 cycloalkyl group, a C6-C14 aryl group, a C3-C8 heteroaryl group, a C1-C3 alkoxy group, a C1-C3 alkylthio group, a C6-C14 arylthio group, a cyano group, a nitro group, a C2-C14 disubstituted amino group and a C2-C14 disubstituted carbamoyl group.

Examples of the halogen atom include the same as described above. Examples of the C3-C6 cycloalkyl group include a cylopropyl group, a cyclopentyl group and a cyclohexyl group. Examples of the C6-C14 aryl group include a phenyl group, a naphthyl group, an anthranyl group and a phenanthryl group. Examples of the C3-C8 heteroaryl group include a pyrrolyl group, a furyl group, a thienyl group, an oxazolyl group, an isoxazolyl group, a thiazolyl group, an imidazolyl group, a pyridyl group, a pyridazyl group, a pyrimidyl group, a benzofuryl group, an indolyl group, a quinolyl group, a quinazolyl group and a purine group. Examples of the C1-C3 alkoxy group include a methoxy group, an ethoxy group and a propoxy group. Examples of the C1-C3 alkylthio group include a methylthio group, an ethylthio group and a propylthio group. Examples of the C6-C14 arylthio group include a phenylthio group and a naphthylthio group. Examples of the C2-C14 disubstituted amino group include a dimethylamino group, a diethylamino group, a diisopropylamino group, a diphenylamino group, a dibenzylamino group and a methylbenzylamino group. Examples of the C2-C14 disubstituted carbamoyl group include a dimethylcarbamoyl group, a diethylcarbamoyl group, a dibenzylcarbamoyl group and a benzylmethylcarbamoyl group.

Specific examples of the alkyl group substituted with the substituent include a bromomethyl group, a chloromethyl group, an iodomethyl group, a fluoromethyl group, a trichloromethyl group, a 2-chloroethyl group, a 2-bromoethyl group, a 2-iodoethyl group, a difluoromethyl group, a trifluoromethyl group, a 2,3-dichloropropyl group, a 2,2-(ditrifluoromethyl)ethyl group, a cyclopropylmethyl group, a cyclopentylmethyl group, a cyclohexylmethyl group, a benzyl group, a 1-naphthylmethyl group, a 2-naphthylmethyl group, a 2-anthranylmethyl group, a N-pyrrolylmethyl group, a 2-furylmethyl group, a 2-thienylmethyl group, a 2-oxazolylmethyl group, a 3-isoxazolylmethyl group, a 2-thiazolylmethyl group, a 2-imidazolylmethyl group, a 4-pyridylmethyl group, a 4-piridazylmethyl group, a 2-pyrimidylmethyl group, a 2-benzofurylmethyl group, a 3-indolylmethyl group, a 2-quinolylmethyl group, a 2-quinazolylmethyl group, a 7-purylmethyl group, a methoxymethyl group, a 2-methoxyethyl group, an ethoxyethyl group, a 2-ethoxyethyl group, a propoxymethyl group, a 2-propoxyethyl group, a methylthiomethyl group, a phenylthiomethyl group, a cyanomethyl group, a nitromethyl group, a dimethylaminomethyl group, a diethylaminomethyl group, a diisopropylaminomethyl group, a diphenylaminomethyl group, a dibenzylaminomethyl group, a methylbenzylaminomethyl group, a dimethylcarbamoylmethyl group, a diethylcarbamoylmethyl group, a dibenzylcarbamoylmethyl group and a benzylmethylcarbamoylmethyl group.

Examples of the alkoxy group include a linear or branched chain C1-C6 alkoxy group such as a methoxy group, an ethoxy group, an n-propoxy group, an isopropoxy group, an n-butoxy group, an isobutoxy group, an n-pentyloxy group and an n-hexyloxy group.

Examples of the alkenyl group include a C2-C6 alkenyl group such as a vinyl group, a 2-propenyl group, a 2-butenyl group, a 2-pentenyl group, a 2-hexenyl group and an allyl group.

Examples of the alkynyl group include a C2-C4 alkynyl group such as a propargyl group and a 1-buten-3-yl group.

Examples of the aryl group include a C6-C14 aryl group such as a phenyl group, a naphthyl group and an anthranyl group.

The aryl group may be substituted with at least one substituent selected from the group consisting of a C1-C6 alkyl group, a C2-C4 alkenyl group, a C5-C6 cycloalkyl group, a halogen atom, a C1-C3 alkoxy group, a C2-C4 alkynyl group, a C2-C14 disubstituted amino group, a nitro group, a cyano group and a C2-C14 disubstituted carbamoyl group.

Examples of the C1-C6 alkyl group include a methyl group, an ethyl group, a propyl group, a butyl group, a pentyl group, a hexyl group, an isopropyl group, an isobutyl group, a sec-butyl group and a tert-butyl group. Examples of the C2-C4 alkenyl group include a vinyl group, a 2-propenyl group, a 2-butenyl group and an allyl group. Examples of the C5-C6 cycloalkyl group include a cylopentyl group and a cyclohexyl group. Examples of the C1-C3 alkoxy group include a methoxy group, an ethoxy group, an n-propoxy group and an isopropoxy group. Examples of the C2-C4 alkynyl group include a propargyl group and a 1-buten-3-yl group. Examples of the halogen atom, a C2-C14 disubstituted amino group and a C2-C14 disubstituted carbamoyl group include the same as described above.

Specific examples of the aryl group substituted with the substituent include a 2-tolyl group, a 3-tolyl group, a 4-tolyl group, a 2-ethylphenyl group, a 4-ethylphenyl group, a 2-propylphenyl group, a 4-propylphenyl group, 2-tert-butylphenyl group, a 4-tert-butylphenyl group, a 2,4,6-tri-tert-butylphenyl group, a 2-pentylphenyl group, a 4-styryl group, a 4-(2-propenyl)phenyl group, a 4-(2-butenyl)phenyl group, a 4-cyclohexylphenyl group, a 4-biphenyl group, a 3-fluorophenyl group, a 3-chlorophenyl group, a pentafluorophenyl group, a 4-methoxyphenyl group, a 4-ethoxyphenyl group, a 4-n-propoxyphenyl group, a 4-isopropoxyphenyl group, a 4-(2-propynyl)phenyl group, a 4-dimethylaminophenyl group, a 4-diethylaminophenyl group, a 4-diisopropylaminophenyl group, a 4-diphenylaminophenyl group, a 4-dibenzylaminophenyl group, a 4-methylbenzylaminophenyl group, a 4-nitrophenyl group, a 4-cyanophenyl group, a 4-dimethylcarbamoylphenyl group, a 4-diethylcarbamoylphenyl group, a 4-dibenzylcarbamoylphenyl group, a 4-benzylmethylcarbamoylphenyl group, a 2-fluoro-1-naphthyl group, a 2-chloro-1-naphthyl group, a 2-nitro-1-naphthyl group and a 1-methyl-2-annthracenyl group.

Examples of the heteroaryl group include a C3-C8 heteroaryl group such as a pyrrolyl group, a furyl group, a thienyl group, an oxazolyl group, an isoxazolyl group, a thiazolyl group, an imidazolyl group, a pyridyl group, a pyridazyl group, a pyrimidyl group, a benzofuryl group, an indolyl group, a quinolyl group, a quinazolyl group, a puryl group, a pyrimidyl group, a thymyl group, a cytosyl group, an adenyl group and a guanyl group.

The heteroaryl group may be substituted with at least one substituent selected from the group consisting of a C1-C4 alkyl group, a benzyl group, a C6-C10 aryl group, a halogen atom, a C1-C3 alkoxy group, a nitro group, a cyano group and a C2-C14 disubstituted amino group.

Examples of the C1-C4 alkyl group include a methyl group, an ethyl group, a propyl group, an isopropyl group and a tert-butyl group. Examples of the C6-C10 aryl group include a phenyl group and a naphthyl group. Examples of the halogen atom, the C1-C3 alkoxy group and the C2-C14 disubstituted amino group include the same as described above.

Specific examples of the heteroaryl group substituted with the substituent include a 1-methyl-2-pyrrolyl group, a 1-tert-butyl-2-pyrrolyl group, a 3-methyl-2-furyl group, a 3-methyl-2-thienyl group, a 4-methyl-2-oxazolyl group, a 4-isopropyl-2-oxazolyl group, a 4-tert-butyl-2-oxazolyl group, a 4-benzyl-2-oxazolyl group, a 4-phenyl-2-oxazolyl group, a 4-naphthyl-2-oxazolyl group, a 4-methyl-2-thiazolyl group, a 4-isopropyl-2-thiazolyl group, a 4-benzyl-2-thiazolyl group, a 1-methyl-2-imidazolyl group, a 1-benzyl-2-imidazolyl group, a 4-dimethylamino-2-pyridyl group, a 4-diethylamino-2-pyridyl group, a 4-diisopropylamino-2-pyridyl group, a 4-dibenzylamino-2-pyridyl group, a 4-methylbenzylamino-2-pyridyl group, a 4,6-difluoro-2-pyrimidyl group, a 4,6-dichloro-2-pyrimidyl group, a 4,6-dibromo-2-pyrimidyl group, a 4,6-diiodo-2-pyrimidyl group, a 2-fluoro-3-benzofuryl group, a 2-methoxy-3-benzofuryl group, a 1-methyl-3-indolyl group, a 1-benzyl-3-indolyl group, a 1-benzyl-2-fluoro-3-indolyl group, a 1-benzyl-4-fluoro-3-indolyl group, a 1-benzyl-5-fluoro-3-indolyl group, a 1-benzyl-5-methoxy-3-indolyl group, a 1-benzyl-2-cyano-3-indolyl group, a 1-benzyl-2-nitro-3-indolyl group, a 5-fluoro-2-quinolyl group, a 5-chloro-2-quinolyl group, a 5-bromo-2-quinolyl group, a 5-ioso-2-quinolyl group, a 5,6-dichloro-2-quinazolyl group, a 8-fluoro-7-puryl group, a 8-chloro-7-puryl group, a 8-bromo-7-puryl group, a 8-iodo-7-puryl group, a 8-cyano-7-puryl group, a 8-nitro-7-puryl group, a 6-fluoro-1-thymyl group, a 6-methoxy-1-thymyl group, a 6-dimethylamino-1-thymyl group, a 6-dibenzylamino-1-thymyl group, a 5-fluoro-citosyl group, a 8-fluoro-9-adenyl group, a 8-methoxy-9-adenyl group, a 8-dimethylamino-9-adenyl group, a 8-fluoro-9-guanyl group, a 8-methoxy-9-guanyl group and a 8-dimethylamino-9-guanyl group.

Examples of the dihydroxypyrimidine compound (1) include 4,6-dihydroxypyrimidine, 2-chloromethyl-4,6-dihydroxypyrimidine, 2-fluoromethyl-4,6-dihydroxypyrimidine, 2-trichloromethyl-4,6-dihydroxypyrimidine, 2-(2-chloroethyl)-4,6-dihydroxypyrimidine, 2-(2-bromoethyl)-4,6-dihydroxypyrimidine, 2-difluoromethyl-4,6-dihydroxypyrimidine, 2-trifluoromethyl-4,6-dihydroxypyrimidine, 2-[2,2-di(trifluoromethyl)ethyl]-4,6-dihydroxypyrimidine, 2-cyclohexylmethyl-4,6-dihydroxypyrimidine, 2-benzyl-4,6-dihydroxypyrimidine, 2-(1-naphthylmethyl)-4,6-dihydroxypyrimidine, 2-(2-anthrylmethyl)-4,6-dihydroxypyrimidine, N-pyrrolylmethyl-4,6-dihydroxypyrimidine, 2-(2-furylmethyl)-4,6-dihydroxypyrimidine, 2-(2-thienylmethyl)-4,6-dihydroxypyrimidine, 2-(2-oxazolylmethyl)-4,6-dihydroxypyrimidine, 2-(2-imidazolylmethyl)-4,6-dihydroxypyrimidine, 2-(4-pyridylmethyl)-4,6-dihydroxypyrimidine, 2-(2-bennzofurylmethyl)-4,6-dihydroxypyrimidine, 2-(3-indolylmethyl)-4,6-dihydroxypyrimidine, 2-(7-purylmethyl)-4,6-dihydroxypyrimidine, 2-methoxymethyl-4,6-dihydroxypyrimidine, 2-methylthiomethyl-4,6-dihydroxypyrimidine, 2-phenylthiomethyl-4,6-dihydroxypyrimidine, 2-cyanomethyl-4,6-dihydroxypyrimidine, 2-nitromethyl-4,6-dihydroxypyrimidine, 2-dimethylaminomethyl-4,6-dihydroxypyrimidine, 2-diisopropylaminomethyl-4,6-dihydroxypyrimidine, 2-dibenzylaminomethyl-4,6-dihydroxypyrimidine, 2-dimethylcarbamoylmethyl-4,6-dihydroxypyrimidine, 2-dibenzylcarbamoylmethyl-4,6-dihydroxypyrimidine, 2-methoxy-4,6-dihydroxypyrimidine, 2-ethoxy-4,6-dihydroxypyrimidine, 2-isopropoxy-4,6-dihydroxypyrimidine, 2-(2-propenyl)-4,6-dihydroxypyrimidine, 2-(1-buten-3-yl)-4,6-dihydroxypyrimidine, 4-tolyl-4,6-dihydroxypyrimidine, 4-ethylphenyl-4,6-dihydroxypyrimidine, 4-propylphenyl-4,6-dihydroxypyrimidine, 2,4,6-tri-tert-butylphenyl-4,6-dihydroxypyrimidine, 2-pentylphenyl-4,6-dihydroxypyrimidine, 4-styryl-4,6-dihydroxypyrimidine, 4-(2-propenyl)phenyl-4,6-dihydroxypyrimidine, 4-(2-butenyl)phenyl-4,6-dihydroxypyrimidine, 4-cyclohexylphenyl-4,6-dihydroxypyrimidine, 2-(4-biphenyl)-4,6-dihydroxypyrimidine, 2-(3-fluorophenyl)-4,6-dihydroxypyrimidine, 2-pentafluorophenyl-4,6-dihydroxypyrimidine, 2-(4-methoxyphenyl)-4,6-dihydroxypyrimidine, 2-(4-dimethylaminophenyl)-4,6-dihydroxypyrimidine, 2-(4-diisopropylaminophenyl)-4,6-dihydroxypyrimidine, 2-(4-nitrophenyl)-4,6-dihydroxypyrimidine, 2-(4-cyanophenyl)-4,6-dihydroxypyrimidine, 2-(4-dimethylcarbamoylphenyl)-4,6-dihydroxypyrimidine, 2-(2-fluoro-1-naphthyl)-4,6-dihydroxypyrimidine, 2-(2-nitro-1-naphthyl)-4,6-dihydroxypyrimidine, 2-(1-methyl-2-anthracenyl)-4,6-dihydroxypyrimidine, 2-(1-methyl-2-pyrrolyl)-4,6-dihydroxypyrimidine, 2-(3-methyl-2-furyl)-4,6-dihydroxypyrimidine, 2-(3-methyl-2-thienyl)-4,6-dihydroxypyrimidine, 2-(4-methyl-2-oxazolyl)-4,6-dihydroxypyrimidine, 2-(4-isopropyl-2-oxazolyl)-4,6-dihydroxypyrimidine, 2-(4-benzyl-2-oxazolyl)-4,6-dihydroxypyrimidine, 2-(4-methyl-2-thiazolyl)-4,6-dihydroxypyrimidine, 2-(4-isopropyl-2-thiazolyl)-4,6-dihydroxypyrimidine, 2-(4-benzyl-2-thiazolyl)-4,6-dihydroxypyrimidine, 2-(1-methyl-2-imidazolyl)-4,6-dihydroxypyrimidine, 2-(4-dimethylamino-2-pyridyl)-4,6-dihydroxypyrimidine, 2-(4,6-dichloro-2-pyrimidyl)-4,6-dihydroxypyrimidine, 2-(2-methoxy-3-benzofuryl)-4,6-dihydroxypyrimidine, 2-(1-benzyl-2-fluoro-3-indolyl)-4,6-dihydroxypyrimidine, 2-(5-fluoro-2-quinolyl)-4,6-dihydroxypyrimidine, 2-(8-fluoro-7-puryl)-4,6-dihydroxypyrimidine, 2-(6-fluoro-1-thymyl)-4,6-dihydroxypyrimidine, 2-(5-fluoro-cytosyl)-4,6-dihydroxypyrimidine, 2-(8-methoxy-9-adenyl)-4,6-dihydroxypyrimidine, 2-(8-dimethylamino-9-guanyl)-4,6-dihydroxypyrimidine, 2-cyano-4,6-dihydroxypyrimidine, 2-nitro-4,6-dihydroxypyrimidine and 2-mercapto-4,6-dihydroxypyrimidine.

As the dihydroxypyrimidine compound (1), a commercially available one may be used and one produced according to known methods may be used.

The process for producing the trichloropyrimidine compound (2) comprising reacting the dihydroxypyrimidine compound (1) with sulfuryl chloride and at least one chlorinating agent selected from the group consisting of hydrogen chloride, thionyl chloride, phosgene, phosphorus oxychloride, phosphorus pentachloride and phosphorus trichloride in the presence of an organic base will be illustrated.

Commercially available sulfuryl chloride is usually used.

The used amount of sulfuryl chloride is usually 1 mole or more per 1 mole of the dihydroxypyrimidine compound (1). There is no specific upper limit thereof, and while the excess amount thereof may be used also to serve as the solvent, it is preferably 1.1 to 4 moles per 1 mole of the dihydroxypyrimidine compound (1).

While at least one chlorinating agent selected from the group consisting of hydrogen chloride, thionyl chloride, phosgene, phosphorus oxychloride, phosphorus pentachloride and phosphorus trichloride is used as the chlorinating agent, phosphorus oxychloride is preferable. Commercially available chlorinating agent is usually used. While the used amount thereof differs depending on kinds of the chlorinating agents, it is usually 0.6 mole or more per 1 mole of the dihydroxypyrimidine compound (1), and there is no specific upper limit. When the chlorinating agent which is a liquid at the reaction temperature is used, the excess amount of the chlorinating agent may be used also to serve as the solvent. One to four moles of the chlorinating agent is preferably used per 1 mole of the dihydroxypyrimidine compound (1).

Examples of the organic base include a tertiary amine such as trimethylamine, triethylamine, diisopropylethylamine and dimethylaniline, and a pyridine compound such as 2-methyl-5-ethylpyridine and pyridine, and the tertiary amine is preferable and triethylamine is more preferable. Commercially available organic base is usually used. The used amount thereof is usually 2 moles or more per 1 mole of the dihydroxypyrimidine compound (1), and while there is no specific upper limit, it is preferably 2 to 4 moles per 1 mole of the dihydroxypyrimidine compound (1).

The reaction is conducted by mixing the dihydroxypyrimidine compound (1), sulfuryl chloride, the chlorinating agent and the organic base, and the mixing order is not particularly limited.

The reaction temperature is usually 50 to 130° C. and preferably 65 to 100° C.

The reaction time is usually 1 to 48 hours.

The reaction may be carried out under normal pressure and under pressure. The progress of the reaction can be checked by a conventional analytical means such as gas chromatography, high performance liquid chromatography, NMR and IR.

After completion of the reaction, the trichloropyrimidine compound (2) can be isolated by being subjected the reaction mixture to conventional aftertreatments such as concentration, extraction and filtration. The isolated trichloropyrimidine compound (2) may be further purified by a conventional purification means such as distillation, column chromatography and recrystallization.

Next, a process for producing the trichloropyrimidine compound (2) by reacting the dihydroxypyrimidine compound (1) with sulfuryl chloride followed by reacting the obtained reaction mixture or a treated material thereof with the above-mentioned chlorinating agent in the presence of an organic base will be illustrated.

The reaction of the dihydroxypyrimidine compound (1) and sulfuryl chloride is usually conducted by mixing the both. The reaction is preferably carried out in the presence of an organic solvent. Examples of the organic solvent include a halogenated aromatic hydrocarbon solvent such as chlorobenzene and dichlorobenzene, an aliphatic hydrocarbon solvent such as pentane, hexane, heptane and cyclohexane, and a halogenated aliphatic hydrocarbon solvent such as dichloromethane, chloroform, carbon tetrachloride and 1,2-dichloroethane. The halogenated aromatic hydrocarbon solvent is preferable and chlorobenzene is more preferable. Two or more kinds of the organic solvent may be mixed to use. While the used amount of the organic solvent is not particularly limited, it is usually 100 parts by weight or less per 1 part by weight of the dihydroxypyrimidine compound (1).

The reaction temperature of the reaction of the dihydroxypyrimidine compound (1) and sulfuryl chloride is usually 0 to 100° C. and preferably 20 to 60° C. The present reaction may be carried out under normal pressure and under pressure.

The progress of the reaction can be checked by conventional analytical means such as gas chromatography, high performance liquid chromatography, NMR and IR.

While the mixing order of the dihydroxypyrimidine compound (1) and sulfuryl chloride is not particularly limited, sulfuryl chloride is preferably added to the dihydroxypyrimidine compound (1).

After completion of the reaction, the obtained reaction mixture may be used as it is for the next reaction, and the reaction mixture is subjected to a conventional aftertreatment such as washing, concentration, filtration and crystallization to obtain a treated material containing a product, and the treated material may be used for the next reaction. Herein, "treated material" may be the product isolated from the reaction mixture.

While at least one chlorinating agent selected from the group consisting of hydrogen chloride, thionyl chloride, phosgene, phosphorus oxychloride, phosphorus pentachloride and phosphorus trichloride is used as the chlorinating agent, phosphorus oxychloride is preferable. Commercially available chlorinating agent is usually used. While the used amount thereof differs depending on kinds of the chlorinating agents, it is usually 0.6 mole or more per 1 mole of the dihydroxypyrimidine compound (1), and there is no specific upper limit. When the chlorinating agent which is a liquid at the reaction temperature is used, the excess amount of the chlorinating agent may be used also to serve as the solvent. One to four moles of the chlorinating agent is preferably used per 1 mole of the dihydroxypyrimidine compound (1).

Examples of the organic base include a tertiary amine such as trimethylamine, triethylamine, diisopropylethylamine and dimethylaniline, and a pyridine compound such as 2-methyl-5-ethylpyridine and pyridine, and the tertiary amine is preferable and triethylamine is more preferable. Commercially available organic base is usually used. The used amount thereof is usually 2 moles or more per 1 mole of the dihydroxypyrimidine compound (1), and while there is no specific upper limit, it is preferably 2 to 4 moles per 1 mole of the dihydroxypyrimidine compound (1).

The reaction temperature of the reaction of the reaction mixture obtained by reacting the dihydroxypyrimidine compound (1) with sulfuryl chloride or the treated material thereof and the chlorinating agent is usually 50 to 130° C. and preferably 65 to 100° C.

The reaction may be carried out under normal pressure and under pressure. The progress of the reaction can be checked by a conventional analytical means such as gas chromatography, high performance liquid chromatography, NMR and IR.

The reaction of the reaction mixture obtained by reacting the dihydroxypyrimidine compound (1) with sulfuryl chloride or the treated material thereof and the chlorinating agent is conducted by mixing the both in the presence of the organic base, and the mixing order is not particularly limited. It is preferred that the reaction mixture obtained by reacting the dihydroxypyrimidine compound (1) with sulfuryl chloride or the treated material thereof is mixed with the chlorinating agent and to the obtained mixture, the organic base is added.

After completion of the reaction, the trichloropyrimidine compound (2) can be isolated by being subjected the reaction mixture to conventional aftertreatments such as concentration, extraction and filtration. The isolated trichloropyrimidine compound (2) may be further purified by a conventional purification means such as distillation, column chromatography and recrystallization.

Examples of the trichloropyrimidine compound (2) include 4,5,6-trichloropyrimidine, 2-chloromethyl-4,5,6-trichloropyrimidine, 2-fluoromethyl-4,5,6-trichloropyrimidine, 2-trichloromethyl-4,5,6-trichloropyrimidine, 2-(2-chloroethyl)-4,5,6-trichloropyrimidine, 2-difluoromethyl-4,5,6-trichloropyrimidine, 2-trifluoromethyl-4,5,6-trichloropyrimidine, 2-cyclohexylmethyl-4,5,6-trichloropyrimidine, 2-benzyl-4,5,6-trichloropyrimidine, 2-(1-naphthylmethyl)-4,5,6-trichloropyrimidine, 2-(2-anthrylmethyl)-4,5,6-trichloropyrimidine, N-pyrrolylmethyl-4,5,6-trichloropyrimidine, 2-(2-oxazolylmethyl)-4,5,6-trichloropyrimidine, 2-(2-imidazolylmethyl)-4,5,6-trichloropyrimidine, 2-(4-pyridylmethyl)-4,5,6-trichloropyrimidine, 2-(3-indolylmethyl)-4,5,6-trichloropyrimidine, 2-(7-purylmethyl)-4,5,6-trichloropyrimidine, 2-methoxymethyl-4,5,6-trichloropyrimidine, 2-(2-methoxyethyl)-4,5,6-trichloropyrimidine, 2-methylthiomethyl-4,5,6-trichloropyrimidine, 2-phenylthiomethyl-4,5,6-trichloropyrimidine, 2-cyanomethyl-4,5,6-trichloropyrimidine, 2-nitromethyl-4,5,6-trichloropyrimidine, 2-dimethylaminomethyl-4,5,6-trichloropyrimidine, 2-dimethylcarbamoylmethyl-4,5,6- trichloropyrimidine, 2-methoxy-4,5,6-trichloropyrimidine, 2-isopropoxy-4,5,6-trichloropyrimidine, 2-(2-propenyl)-4,5,6-trichloropyrimidine, 2-(1-buten-3-yl)-4,5,6-trichloropyrimidine, 4-tolyl-4,5,6-trichloropyrimidine, 4-ethylphenyl-4,5,6-trichloropyrimidine, 4-styryl-4,5,6-trichloropyrimidine, 4-(2-butenyl)phenyl-4,5,6-trichloropyrimidine, 2-(4-biphenyl)-4,5,6-trichloropyrimidine, 2-(3-fluorophenyl)-4,5,6-trichloropyrimidine, 2-pentafluorophenyl-4,5,6-trichloropyrimidine, 2-(4-methoxyphenyl)-4,5,6-trichloropyrimidine, 2-(4-dimethylaminophenyl)-4,5,6-trichloropyrimidine, 2-(4-diisopropylaminophenyl)-4,5,6-trichloropyrimidine, 2-(4-nitrophenyl)-4,5,6-trichloropyrimidine, 2-(4-cyanophenyl)-4,5,6-trichloropyrimidine, 2-(4-dimethylcarbamoylphenyl)-4,5,6-trichloropyrimidine, 2-(2-fluoro-1-naphthyl)-4,5,6-trichloropyrimidine, 2-(2-nitro-1-naphthyl)-4,5,6-trichloropyrimidine, 2-(1-methyl-2-anthracenyl)-4,5,6-trichloropyrimidine, 2-(1-methyl-2-pyrrolyl)-4,5,6-trichloropyrimidine, 2-(3-methyl-2-furyl)-4,5,6-trichloropyrimidine, 2-(3-methyl-2-thienyl)-4,5,6-trichloropyrimidine, 2-(4-methyl-2-oxazolyl)-4,5,6-trichloropyrimidine, 2-(4-isopropyl-2-oxazolyl)-4,5,6-trichloropyrimidine, 2-(4-benzyl-2-oxazolyl)-4,5,6-trichloropyrimidine, 2-(4-methyl-2-thiazolyl)-4,5,6-trichloropyrimidine, 2-(4-isopropyl-2-thiazolyl)-4,5,6-trichloropyrimidine, 2-(4-benzyl-2-thiazolyl)-4,5,6-trichloropyrimidine, 2-(1-methyl-2-imidazolyl)-4,5,6-trichloropyrimidine, 2-(4-dimethylamino-2-pyridyl)-4,5,6-trichloropyrimidine, 2-(4,6-dichloro-2-pyrimidyl)-4,5,6-trichloropyrimidine, 2-(2-methoxy-3-benzofuryl)-4,5,6-trichloropyrimidine, 2-(1-benzyl-2-fluoro-3-indolyl)-4,5,6-trichloropyrimidine, 2-(5-fluoro-2-quinolyl)-4,5,6-trichloropyrimidine, 2-(8-fluoro-7-puryl)-4,5,6-trichloropyrimidine, 2-(6-fluoro-1-thymyl)-4,5,6-trichloropyrimidine, 2-(5-fluoro-cytosyl)-4,5,6-trichloropyrimidine, 2-(8-methoxy-9-adenyl)-4,5,6-trichloropyrimidine, 2-(8-dimethylamino-9-guanyl)-4,5,6-trichloropyrimidine, 2-cyano-4,5,6-trichloropyrimidine, 2-mercapto-4,5,6-trichloropyrimidine and 2-nitro-4,5,6-trichloropyrimidine.

EXAMPLES

The present invention will be illustrated in more detail by Examples below. The present invention is not limited to these Examples.

Example 1

To a 100 ml three-neck flask, 5.0 g of 4,6-dihydroxypyrimidine and 34.2 g of phosphorus oxychloride were added. The obtained mixture was adjusted at 30° C., and then, 12.04 g of sulfuryl chloride was added dropwise thereto. The obtained mixture was maintained at the same temperature for 3 hours, and then, 9.0 g of triethylamine was added dropwise thereto. The obtained mixture was maintained at 85° C. for 16 hours. The obtained reaction mixture was cooled to room temperature, and 50 g of toluene was added thereto. Twenty point five grams of warm water adjusted at 40° C. was further added thereto followed by separating to an organic layer and an aqueous layer. The obtained organic layer was washed with 15 g of 5% aqueous sodium hydroxide solution and further washed with 15 g of water. The obtained organic layer was concentrated to obtain 104.7 g of a solution containing 4,5,6-trichlorpyrimidine. The solution was analyzed by high performance liquid chromatography internal standard method, and the content of 4,5,6-trichlorpyrimidine was 3.7% and the yield was 47%.

Example 2

To a 1000 mL four-neck flask, 89.7 g of 4,6-dihydroxypyrimidine and 179.3 g of chlorobenzene were added. The obtained mixture was adjusted at 40° C., and then, 129.6 g of sulfuryl chloride was added dropwise thereto over 1 hour. The obtained mixture was maintained at the same temperature for 6 hours. To the obtained reaction mixture, 269.9 g of phosphorus oxychloride was added at the same temperature. Further, 178.1 g of triethylamine was added dropwise thereto over 2 hours at an inner temperature of 40 to 80° C. After completion of the addition, the obtained mixture was maintained at 83° C. for 10 hours. The obtained reaction mixture was cooled to room temperature. To another 100 mL four-neck flask, 269.0 g of water was added followed by adjusting at 40° C. To it, the obtained reaction mixture was added dropwise over 30 minutes. The inner temperature during the addition was 30 to 50° C. The obtained mixture was filtrated using Radiolite (registered trademark) and the obtained filtrate was separated to an organic layer and an aqueous layer. The aqueous layer was extracted with 44.8 g of chlorobenzene, and the obtained chlorobenzene layer was mixed with the previously obtained organic layer. The organic layer after mixing was washed with 44.8 g of water and then, concentrated under reduced pressure to obtain 169.2 g of black oily matter. The oily matter was analyzed by high performance liquid chromatography internal standard method, and 126.9 g of 4,5,6-trichlorpyrimidine was containd in the oily matter. The yield was 86%.

Example 3

To a 1000 mL four-neck flask, 90.0 g of 4,6-dihydroxypyrimidine and 180.0 g of chlorobenzene were added. The obtained mixture was adjusted at 40° C., and then, 130.0 g of sulfuryl chloride was added dropwise thereto over 20 minutes. The obtained mixture was maintained at the same temperature for 8 hours. To the obtained reaction mixture, 271.0 g of phosphorus oxychloride was added over 30 minutes at the same temperature. Further, 178.7 g of triethylamine was added dropwise thereto over 90 minutes at an inner temperature of 40 to 75° C. After completion of the addition, the obtained mixture was maintained at 85° C. for 10 hours. The obtained reaction mixture was cooled to 27° C., and 270.0 g of water was added dropwise thereto over 30 minutes. The inner temperature during the addition was 40 to 50° C. The obtained mixture was stirred for 1 hour at the same temperature and was separated to an organic layer and an aqueous layer. The aqueous layer was extracted with 90.0 g of chlorobenzene, and the obtained chlorobenzene layer was mixed with the previously obtained organic layer. The organic layer after mixing was washed with 45.0 g of water to obtain 395.6 g of a solution containing 4,5,6-trichlorpyrimidine. The solution was analyzed by high performance liquid chromatography internal standard method, and 119.2 g of 4,5,6-trichlorpyrimidine was included in the solution. The yield was 81%.

Three hundred ninety five point six grams of the obtained solution was concentrated at 6.7 kPa and the obtained oily matter was distilled at 91° C. and 1.3 kPa to obtain 104.0 g of 4,5,6-trichlorpyrimidine (purity: 99.6%).

Industrial Applicability

According to the present invention, a 4,5,6-trichloropyrimidine compound, which is useful as an intermediate of pharmaceuticals and agrichemicals, can be produced in a good yield.

The invention claimed is:

1. A process for producing a trichloropyrimidine compound represented by the formula (2):

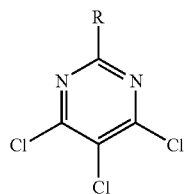

(2)

wherein R represents a hydrogen atom; a halogen atom; a mercapto group; a cyano group; a nitro group; an alkyl group which may be substituted with at least one substituent selected from the group consisting of a halogen atom, a C3-C6 cycloalkyl group, a C6-C14 aryl group, a C3-C8 heteroaryl group, a C1-C3 alkoxy group, a C1-C3 alkylthio group, a C6-C14 arylthio group, a cyano group, a nitro group, a C2-C14 disubstituted amino group and a C2-C14 disubstituted carbamoyl group; an alkoxy group; an alkenyl group; an alkynyl group; an aryl group which may be substituted with at least one substituent selected from the group consisting of a C1-C6 alkyl group, a C2-C4 alkenyl group, a C5-C6 cycloalkyl group, a halogen atom, a C1-C3 alkoxy group, a C2-C4 alkynyl group, a C2-C14 disubstituted amino group, a nitro group, a cyano group and a C2-C14 disubstituted carbamoyl group; or a heteroaryl group which may be substituted with at least one substituent selected from the group consisting of a C1-C4 alkyl group, a benzyl group, a C6-C10 aryl group, a halogen atom, a C1-C3 alkoxy group, a nitro group, a cyano group and a C2-C14 disubstituted amino group, comprising reacting a dihydroxypyrimidine compound represented by the formula (1):

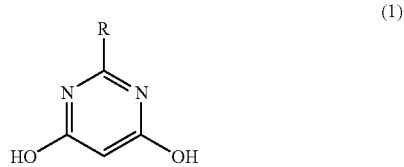

(1)

wherein R represents the same meaning as above, with sulfuryl chloride and at least one chlorinating agent selected from the group consisting of hydrogen chloride, thionyl chloride, phosgene, phosphorus oxychloride, phosphorus pentachloride and phosphorus trichloride in the presence of an organic base.

2. The process according to claim 1, wherein the dihydroxypyrimidine compound represented by the formula (1) is reacted with sulfuryl chloride, and the obtained reaction mixture or a treated material thereof is reacted with at least one chlorinating agent selected from the group consisting of hydrogen chloride, thionyl chloride, phosgene, phosphorus oxychloride, phosphorus pentachloride and phosphorus trichloride in the presence of an organic base.

3. The process according to claim 1, wherein the organic base is triethylamine.

4. The process according to claim 2, wherein the reaction of the dihydroxypyrimidine compound represented by the formula (1) and sulfuryl chloride is conducted in the presence of an organic solvent.

5. The process according to claim 4, wherein the organic solvent is chlorobenzene.

6. The process according to claim 1, wherein the chlorinating agent is phosphorus oxychloride.

7. The process according to claim 1, wherein R is a hydrogen atom.

8. The process according to claim 2, wherein the organic base is triethylamine.

9. The process according to claim 2, wherein the chlorinating agent is phosphorus oxychloride.

10. The process according to claim 2, wherein R is a hydrogen atom.

* * * * *